United States Patent [19]

Paolino

[11] 4,245,626

[45] Jan. 20, 1981

[54] AUTOMATIC COCKING DEVICE FOR PELVIC SUPPORT SECTION OF CHIROPRACTIC TABLE

[76] Inventor: Charles M. Paolino, 235 Forest Ave., Emerson, N.J. 07630

[21] Appl. No.: 98,383

[22] Filed: Nov. 29, 1979

[51] Int. Cl.[3] .............. A61F 5/00

[52] U.S. Cl. .............. 128/70

[58] Field of Search .............. 128/69, 70, 71, 72, 128/73, 74; 269/322-328

[56] References Cited

U.S. PATENT DOCUMENTS

| | | | |
|---|---|---|---|
| 2,749,911 | 6/1956 | Griffin | 128/70 |
| 3,420,229 | 1/1969 | Miller | 128/71 |
| 3,830,233 | 8/1974 | Hill | 128/71 |
| 3,998,218 | 12/1976 | Lane et al. | 128/70 |
| 4,050,454 | 9/1977 | Ekholm | 128/70 |

*Primary Examiner*—John D. Yasko
*Attorney, Agent, or Firm*—Robert A. Maikis

[57] ABSTRACT

An automatic cocking device is provided for a chiropractic table of the type having a pivotally mounted pelvic support section which is adapted to be cocked to an elevated position by rotation of a cocking shaft and adapted to be tripped to a dropped position by chiropractic thrusts. The cocking device has an electric motor which is connected through a speed reducing gear train and an eccentric mechanical linkage to a crank which is mounted on the cocking shaft of the table, so that the cocking shaft is rotated to cock the pelvic support section. The electric motor is controlled by a parallel-connected circuit having at least one foot-operated switch and a cam follower switch which is actuated by a cam driven by the output shaft of the speed reducer, so that the output shaft which drives the eccentric linkage makes substantially one full revolution upon actuation of the foot-operated switch. Support brackets and mounting clamps permit field installation of the automatic cocking device on existing tables having manually-operated cocking devices.

11 Claims, 8 Drawing Figures

AUTOMATIC COCKING DEVICE FOR PELVIC SUPPORT SECTION OF CHIROPRACTIC TABLE

BACKGROUND OF THE INVENTION

1. Field of the Invention

This invention relates to chiropractic tables and more particularly to an automatic cocking device for the pelvic support section of such chiropractic tables.

2. Description of the Prior Art

In the practice of chiropractic, the practitioner is called upon to make adjustments to the human spinal column to treat an impaired or abnormal position of one or more vertebrae which could cause a disturbance to the nervous system or interfere with normal nerve supply. The patient is often treated on a chiropractic table which is specially designed to facilitate such spinal adjustments. When the treatment involves adjustments of the pelvic-lumbar portion of the spine, the chiropractic table may be provided with a pelvic support section which supports the pelvis and legs of the patient. The pelvic support section is pivotally mounted at one end thereof to permit the other end thereof to be cocked to an elevated position, so that when the spinal adjustment is made by applying a pelvic thrust to the patient's spinal column, the impact of the thrust force on the patient is lessened by permitting the pelvic support section to be tripped or dropped to its unelevated position by the force of the practitioner's adjustment. This pelvic drop feature of chiropractic tables minimizes the traumatic effect of the adjustment on the patient.

The chiropractic tables available at the present time are customarily supplied with a manually-operable cocking device to elevate the pelvic support section of the table by moving a hand lever which rotates a cocking shaft to elevate the pelvic support section. Since the chiropractor usually makes a minimum of three pelvic thrusts or applications of force to the patient's spinal column for lumbar-pelvic spinal adjustments, it is apparent that the manually-operable cocking of the pelvic support section prior to each pelvic thrust is both time consuming and tiring to the doctor of chiropractic. The practitioner must remove his hands from the patient-'back to operate the manual cocking lever, so that the specific vertebrae and pelvic structure involved in the spinal adjustment must be again located and reset by the practitioner prior to the pelvic thrust. Apart from the time consuming aspect of such manual operation, the procedure may cause patient apprehension and there is a possibility of loss of a previously accurate spinal structure contact.

In order to avoid the above difficulties, it would be desirable to provide a motorized or automatic cocking device for the table. However, the installation of such automatic devices on existing tables in difficult because there is a limited space available in which the component parts of the device may be located without interfering with the required operation of the various parts of the table. Furthermore, since the number of suitable attachment points for automatic cocking devices to existing tables is imited, it is essential that installation be made without relocating the existing parts. Additionally, the automatic device should produce a gentle cocking of the pelvic support section which will not injure or disturb the patient. Finally, a suitable automatic device should be capable of easy field installation on chiropractic tables having manual cocking devices without impairing the function of the manual cocking device.

SUMMARY OF THE INVENTION

It is an object of this invention to provide an automatic cocking device for the pelvic support section of chiropractic tables wherein the device may be easily installed in the limited space available for such installations without interference with normal table operation or the relocation of existing table parts.

It is a further object of this invention to provide an automatic cocking device for the pelvic support section of chiropractic tables wherein the device is not only reliable in operation but also provides a gentle cocking action.

It is a still further object of this invention to provide an automatic cocking device for chiropractic tables wherein the device is adapted for field installation on existing chiropractic tables having manual cocking devices without impairing the function of the manual cocking device.

Briefly, the automatic cocking device of the invention may be used with chiropractic tables of the type having a pelvic support section which is pivotally mounted to permit cocking to an elevated position by rotation of a cocking shaft through a predetermined angle of rotation and tripping to a dropped position by chiropractic pelvic thrusts. The cocking device comprises motor means mounted on the table and having a rotary output shaft. Lever means are mounted on the cocking shaft for rotation thereof and mechanical linkage means are connected between the motor means output shaft and the lever means for converting the rotary motion of the motor shaft to substantially unidirectional linear motion at the lever means, to thereby rotate the cocking shaft through the predetermined angle of rotation and cock the pelvic support section. Motor control means are coupled to the motor means for starting and stopping the motor means to cock the pelvic support section. The lever means may comprise a crank, while the mechanical linkage means may take the form of an eccentric having a rotatable disk member with an eccentrically mounted pin thereon and a longitudinally-extending connecting member having one end thereof pivotally mounted on the pin and the other end thereof mounted on the crank. The disk member is connected to the output shaft of the motor means for rotation thereby. The motor control means may comprise foot-operated switch means for energizing the motor means to cause rotation of the output shaft thereof and position-responsive switch means responsive to the angular position of the motor means output shaft for deenergizing the motor means at a predetermined angular position of the motor means output shaft, so that the output shaft makes substantially one full revolution of 360° after energization of the motor means.

The nature of the invention and other objects and additional advantages thereof will be more readily understood by those skilled in the art after consideration of the following detailed description taken in conjunction with the accompanying drawings.

DESCRIPTION OF THE PREFERRED EMBODIMENT OF THE INVENTION

Figure 1:
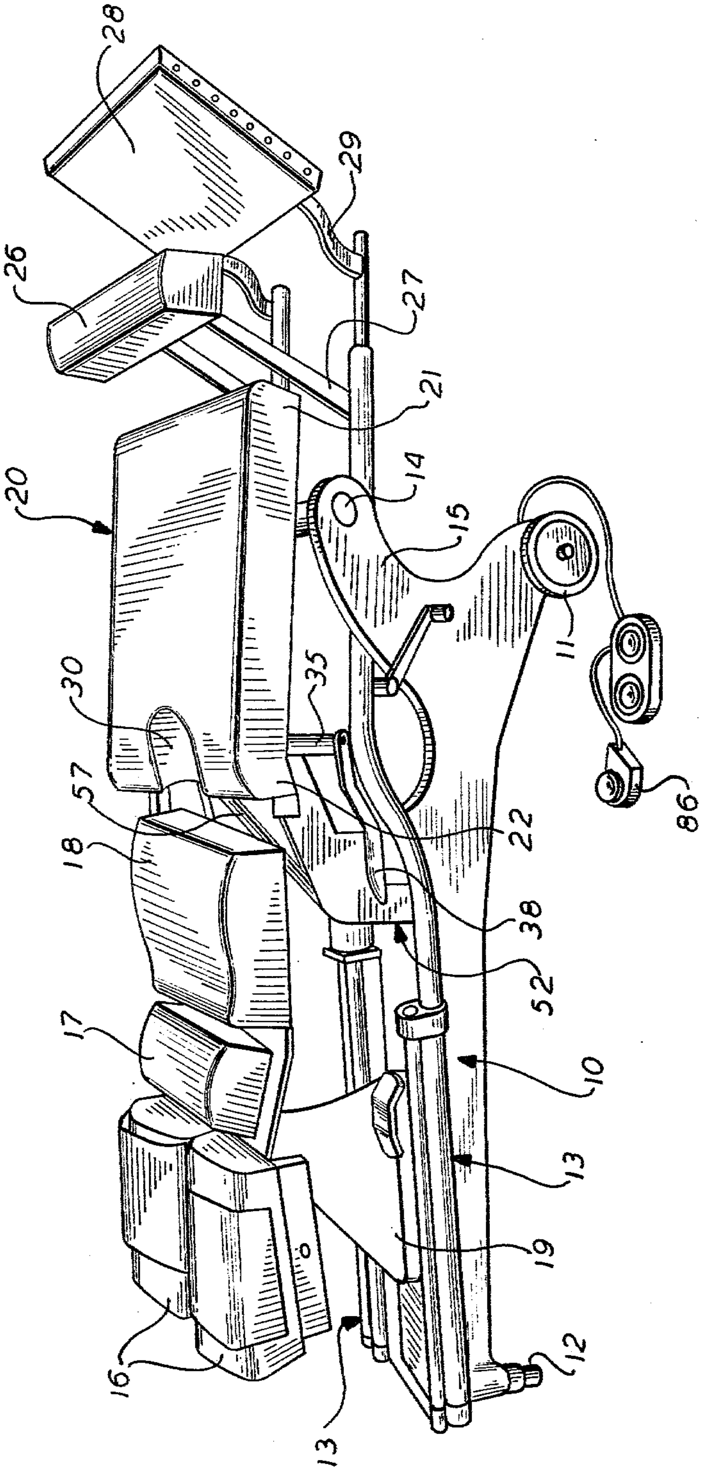
FIG. 1 is a perspective view of a chiropractic table having an automatic cocking device for the pelvic support section thereon constructed in accordance with the teachings of the present invention.
Figures 2, 3:
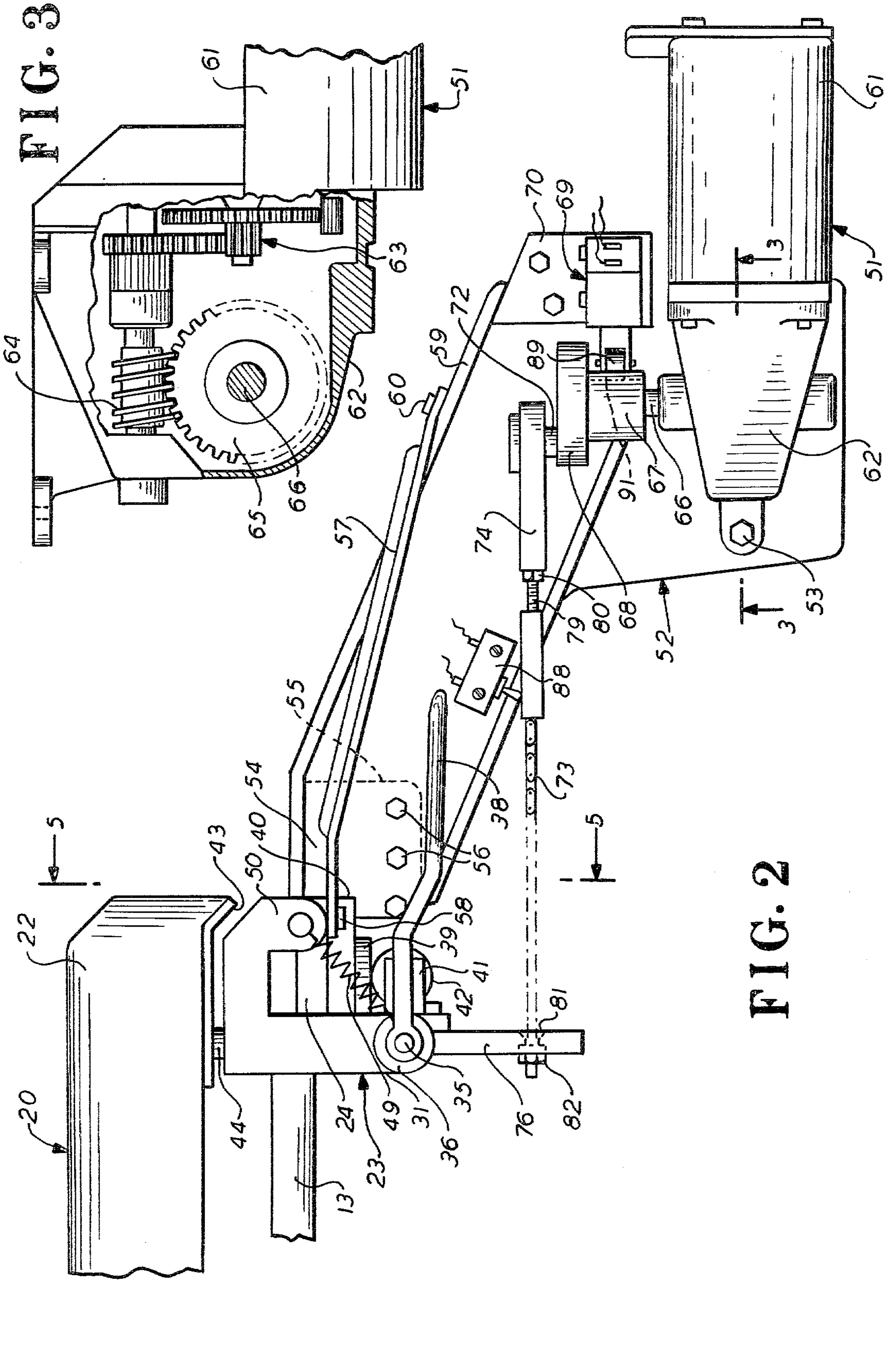
FIG. 2 is a side elevational view of the pelvic support section of the table of FIG. 1 with the automatic cocking device mounted thereon.
FIG. 3 is a partial sectional view taken along the line 3—3 of FIG. 2 of the drawings showing a speed reducing gear train employed in the cocking device of the invention.
Figure 5:
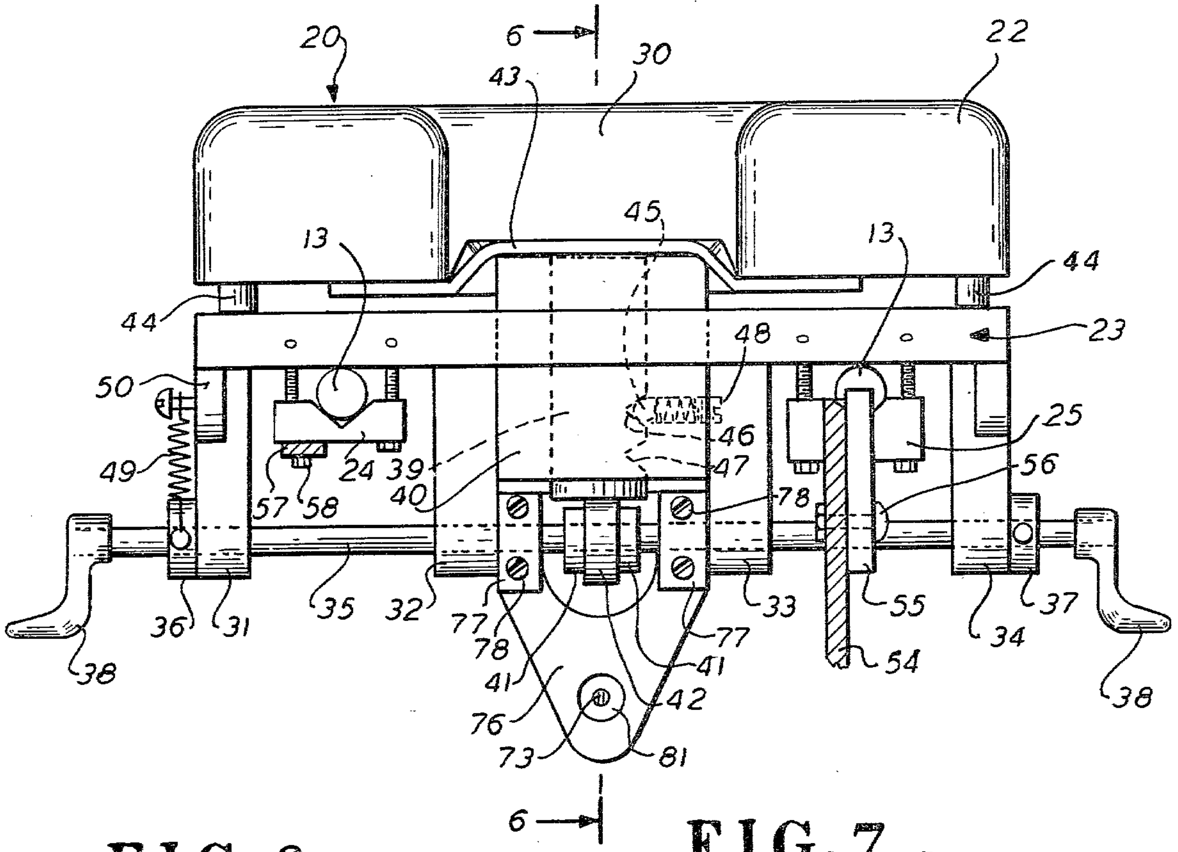
FIG. 5 is a full sectional view of the cocking device of the invention taken along the line 5—5 of FIG. 2 of the drawings.

Referring now to FIG. 1 of the drawings, there is shown a chiropractic table of a type commerically available at the present time having the automatic cocking device of the invention mounted thereon. The table comprises a base, indicated generally as 10, having wheels 11 and support legs 12 thereon. A support frame formed by a pair of support rails, indicated generally as 13, is pivotally mounted on the base 10 for rotation about a main support shaft 14 which is mounted in a pair of upwardly-extending arms 15 of the base. The support rails 13 are suspended from the main shaft 14 by a support yoke (now shown). The table is provided with a head support section 16, a chest support section 17 and an abdominal support section 18 which are separately adjustable by means not shown and which are mounted on the support rails 13 by means of an upwardly-extending support pedestal 19. A pelvic support section, indicated generally as 20, has one end 21 thereof pivotally mounted on the support rails 13 by means not shown and the other end 22 thereof supported by a laterally-extending support member, indicated generally as 23, which is mounted on the support rails 13 by means of a first clevis 24 and a second clevis 25 as shown in FIGS. 2 and 5 of the drawings. An ankle support section 26 is mounted on the support rails 13 by means of upwardly-extending brackets 27 and a foot support platform 28 is similarly mounted on the rails by means of brackets 29.

From the foregoing description, it is apparent that all of the patient support sections 16, 17, 18, 20, 26 and 28 are mounted on the support frame formed by the support rails 13, so that all of these sections may be rotated with the support frame about the central shaft 14. By virtue of this arrangement, a patient lying face down on the table with his feet abutting the foot support platform 28 may be rotated from a horizontal position to almost a standing position by manual or power-operated means (not shown). In practice, the patient support sections 16, 17, 18, 20 and 26 usually comprise cushions so that the patient on the table is comfortable and assumes a relaxed position.

Figure 6:
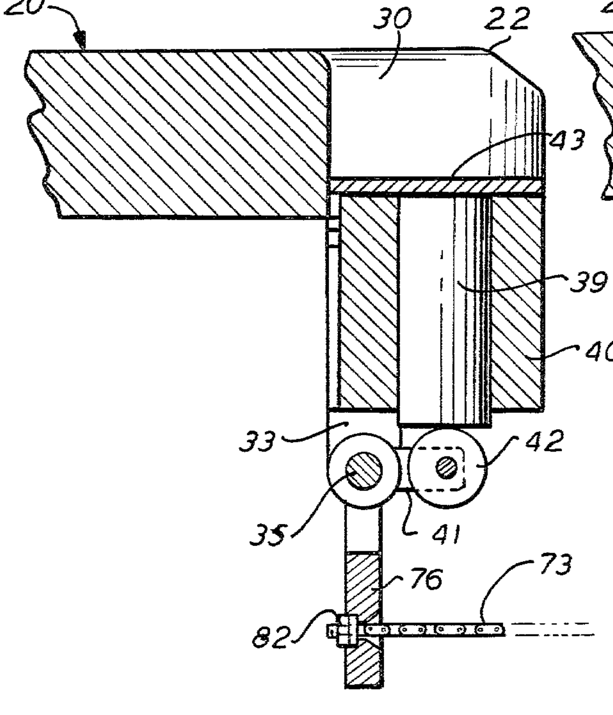
FIG. 6 is a full sectional view of the cocking device taken along the line 6—6 of FIG. 5 of the drawings showing the pelvic support section tripped to its dropped position.
Figure 7:
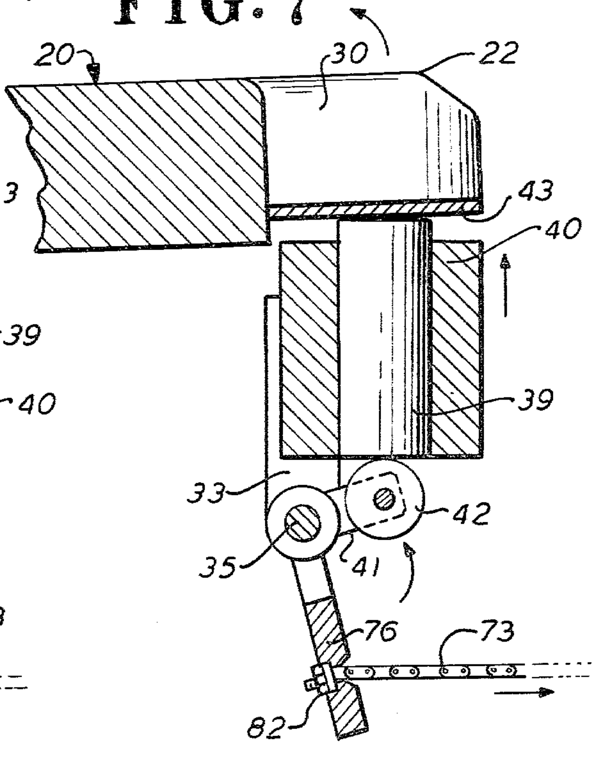
FIG. 7 is a full sectional view of the cocking device taken along the line 6—6 of FIG. 5 of the drawings showing the pelvic support section cocked to its elevated position.

The pelvic support section 20 is intended to accomodate the pelvic area and legs of the patient and is provided with a cut away portion 30 at the end 22 thereof. The pivotal mounting of the end 21 of the pelvic support section enables the end 22 of that section to be rotated with respect to the support frame of the table, so that the end 22 may be elevated a relatively small distance, such as $\frac{5}{8}$", for example, with respect to the lateral support member 23 on which the end 22 normally rests. In order to accomplish this, the table has a manually-operable cocking device which cocks the pelvic support section to its elevated position where it is held in place unitl the force of a pelvic thrust by the chiropractor trips the pelvic support section to a dropped position where it rests against the laterally-extending member 23. The manual cocking device is shown in FIGS. 2, 5, 6 and 7 of the drawings wherein it is seen that the support member 23 has four, downwardly-extending trunnions 31, 32, 33 and 34 which support and receive a rotatable cocking shaft 35. The cocking shaft 35 is restrained from axial movement by means of collars 36 and 37. Manual operating levers 38 are provided on opposite ends of the cocking shaft for actuation by the chiropractor. As seen in FIGS. 5, 6 and 7 of the drawings, a cylindrical cocking plunger 30 is slideably disposed in a boss 40 formed on the laterally-extending support member 23 between the trunnions 32 and 33. The cocking shaft 35 has a pair of outwardly-extending support arms 41 mounted thereon for rotation with the shaft between the trunnions 32 and 33. A cylindrical roller 42 is rotatably mounted at the ends of the arms 41 so that as the cocking lever 38 is rotated in a counterclockwise direction as seen in FIG. 2 of the drawings, the roller 42 will engage the bottom of the plunger 39 and slide it upwardly in the boss 40 to elevate the end 22 of the pelvic support section 20 to its elevated or cocked position.

The cut away portion 30 of the pelvic support section is provided with a metal plate 43 to engage the top of the cocking plunger 39. A pair of rubber bumpers 44 are mounted on the top of the support member 23 to cushion the shock when the pelvic support section 20 is tripped to its dropped position. The cocking plunger 39 may be held in either of its cocked and tripped positions by any convenient means, such as the detent means shown in FIG. 5 of the drawings, for example, wherein a spring-loaded ball 45 engages one or the other of detents 46 and 47 formed in the plunger 39. When the cocking lever 38 is rotated to cock the pelvic support section, the upward movement of the plunger 39 forces the ball 45 out of engagement with detent 46 against the action of the spring. When the plunger 39 moves up, the spring-loaded ball 45 engages the detent 47 so that when the cocking lever 38 is released, the detent holds the pelvic support section in the elevated or cocked position. When the pelvic support section is in the cocked position, the chiropractor applies a pelvic thrust to the patient and the resulting force on the top of the plunger 39 causes it to move down and to force the ball 45 out of engagement with the detent 47 until it is again seated in the detent 46. Means, such as the screw 48 shown in FIG. 5 of the drawings, may be provided to adjust the spring pressure on the ball 45 to thereby adjust the force required to trip the pelvic support section to its dropped position, whereby factors, such as the weight of the patient, may be compensated for in administering a pelvic thrust or adjustment. As seen in FIGS. 2 and 5, a helical spring 49 is connected between the collar 36 on the cocking shaft 35 and a lug 50 formed on the latterally-extending support member 23, so that the cocking lever 38 is maintained in a substantially horizontal position.

From the foregoing description of the manual cocking devices available on present day chiropractic tables, it is apparent that little space is available for the installation of an automatic cocking device. For example, only limited lateral space is available underneath the cocking plunger 39 to permit a suitably large electric motor or solenoid to be installed to raise it to its elevated position. Furthermore, electric solenoids operate almost instantaneously when they are energized and the application of such a quick upward thrust to the pelvic support section 20 could prove injurious to the patient and would, in any event, not be conducive to the calm state of mind desired for optimum chiropractic treatment.

Figure 4:
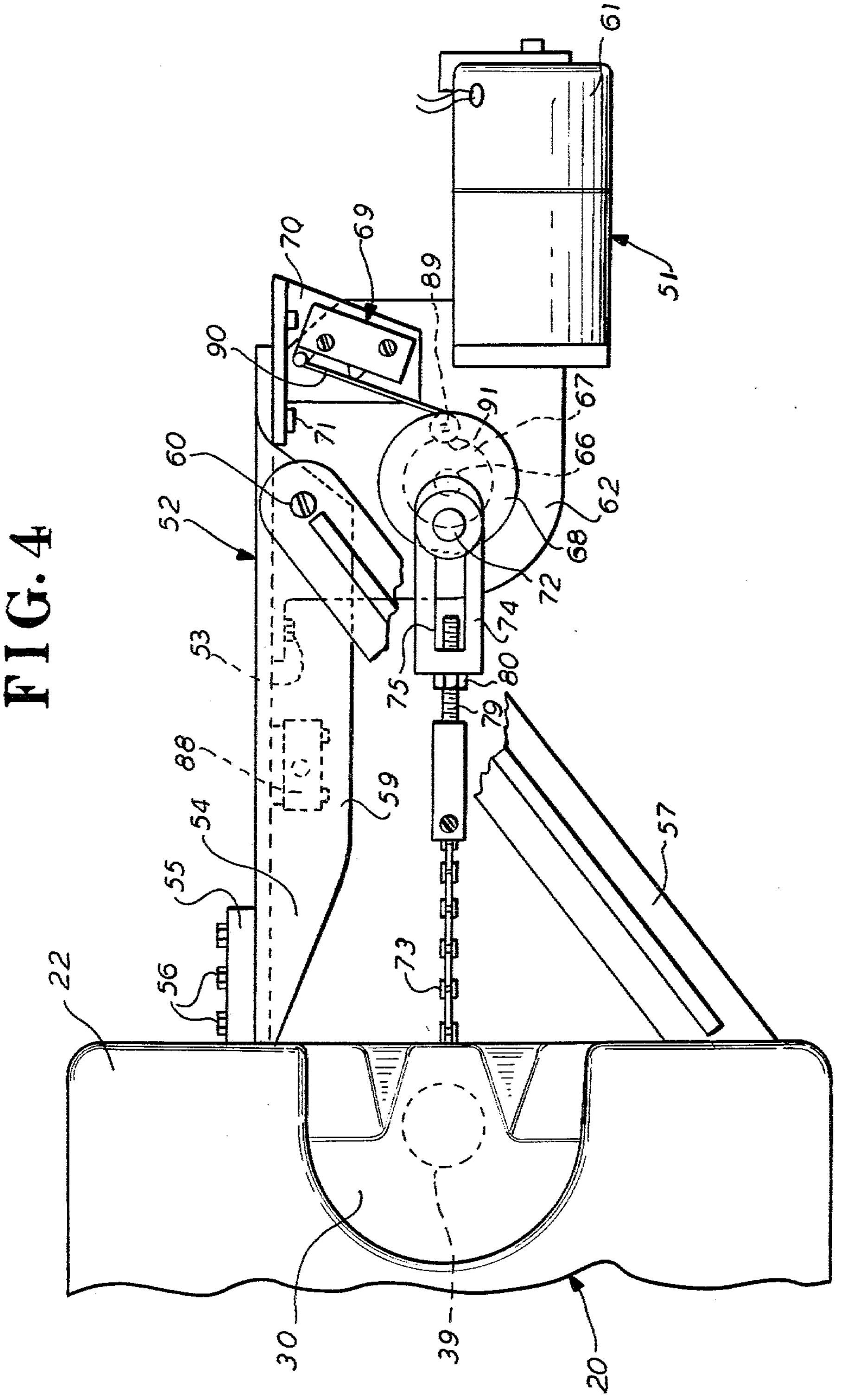
FIG. 4 is a top plan view of the automatic cocking device of the invention with a portion of a lateral support brace broken away to reveal details of construction.

As seen in FIGS. 2, 4 and 5 of the drawings, the automatic cocking device of the invention comprises electric motor means, indicated generally as 51, which is mounted on a downwardly-sloping support bracket, indicated generally as 52, by means such as bolts 53. The upper end 54 of the support bracket is mounted on an outwardly-extending lug or projection 55 of the clevis 25 by means such as bolts 56, so that the motor means 51 and the bracket 52 are securely mounted on the laterally-extending support member 23 which is in turn mounted on the support frame formed by the support rails 13. A laterally-extending cross brace 57 has one end thereof mounted on the clevis 24 by means of a bolt 58 and the other end thereof mounted on a flange 59 on the support bracket 52 by means such as a screw 60, so that good lateral support is provided for support bracket 52. As seen in FIGS. 2 and 3 of the drawings, the electric motor means 51 comprises an electric motor 61 having a rotary output shaft and a speed-reducing gear train 62 which is connected to the output shaft of the motor. The speed reducer 62 has a gear train, indicated generally as 63, which connects the motor output shaft to a worm gear 64 which drives a spur gear 65 which is mounted on the output shaft 66 of the motor means 51. The worm and spur gear provide a right angle drive. The electric motor and speed-reducing gear train may comprise a commercially-available integral assembly which is available in several motor sizes and speed-reducing gear ratios.

The output shaft 66 of the motor means 51 has mounted thereon a rotatable cam 67 and a rotatable disk member 68 which may comprise a circular or non-circular disk, as desired. For reasons hereinafter described, the cam 67 drives a cam follower switch, indicated generally as 69, which is mounted on a small bracket 70 which is in turn mounted on support bracket 52 by means of bolt 71. The rotatable disk member 68 has a pin 72 eccentrically mounted thereon. A longitudinally-extending connecting member 73 which may comprise a flexible chain has one end thereof pivotally mounted on the pin 72 by means of a shackle 74 having an elongated slot 75 therein which receives the pin. The other end of the connecting member 73 is mounted on one end of a bifurcated crank 76 having two arms which are disposed between the trunnions 32 and 33 and on opposite sides of the roller 42 as seen in FIG. 5 of the drawings. The arms of the crank 76 are secured to the cocking shaft 35 by means of mounting straps 77 and screws 78 which function as clamping means, so that rotational movement of the crank 76 will cause the cocking shaft 45 to rotate. The disk 68, the pin 72 and the longitudinally-extending connecting member 73 form mechanical linkage means which function as an eccentric to convert the rotary motion of the motor means output shaft 66 to substantially unidirectional linear motion at the end of connecting member 73 which is mounted on the crank or lever means 76.

By virtue of this arrangement, when the disk member 68 is rotated through one full revolution of 360° starting from the angular position shown in FIG. 4 of the drawings, the pin 72 will reach the opposite side of the disk when the disk has made one-half revolution of 180°, so that the chain 73 will be pulled with substantially linear motion a distance which is required to rotate the crank 76 through the predetermined angle of rotation which is needed to cock the pelvic support section to its elevated position as shown in FIGS. 6 and 7 of the drawings. The remaining 180° of disk rotation will cause the pin 72 to return to its original position. However, since the connecting member 73 is a flexible chain, the resulting substantially linear movement of the pin will not be transmitted back to the crank 76, so that the described eccentric is operable only to cause unidirectional rotation of the cocking shaft in the direction required to cock the pelvic support section. The active length of the connecting member or chain 73 may be adjusted by a threaded shaft 79 and nut 80 at the end of the chain which is connected to the shackle 74, so that the angle of rotation of the cocking shaft 35 may be adjusted as required. The other end of the chain 73 may be mounted on the crank 76 by any convenient means, such as passing the end through an opening 81 in the crank and securing it with a stop member 82 as illustrated. If desired, the flexible chain 73 could be replaced by a relatively inflexible rod having one end thereof pivotally mounted on the pin 72 and the other end thereof slidably disposed in the opening 81 in the crank 76. In this arrangement, the stop means 82 on the end of the rod which is disposed in the opening 81 would prevent that end of the rod from being pulled through the opening 81 during the first half-revolution of the disk 68, but would permit the rod to be pushed back through the opening 81 during the last half-revolution of the disk, so that the required unidirectional rotation of the cocking shaft would still be obtained.

Figure 8:
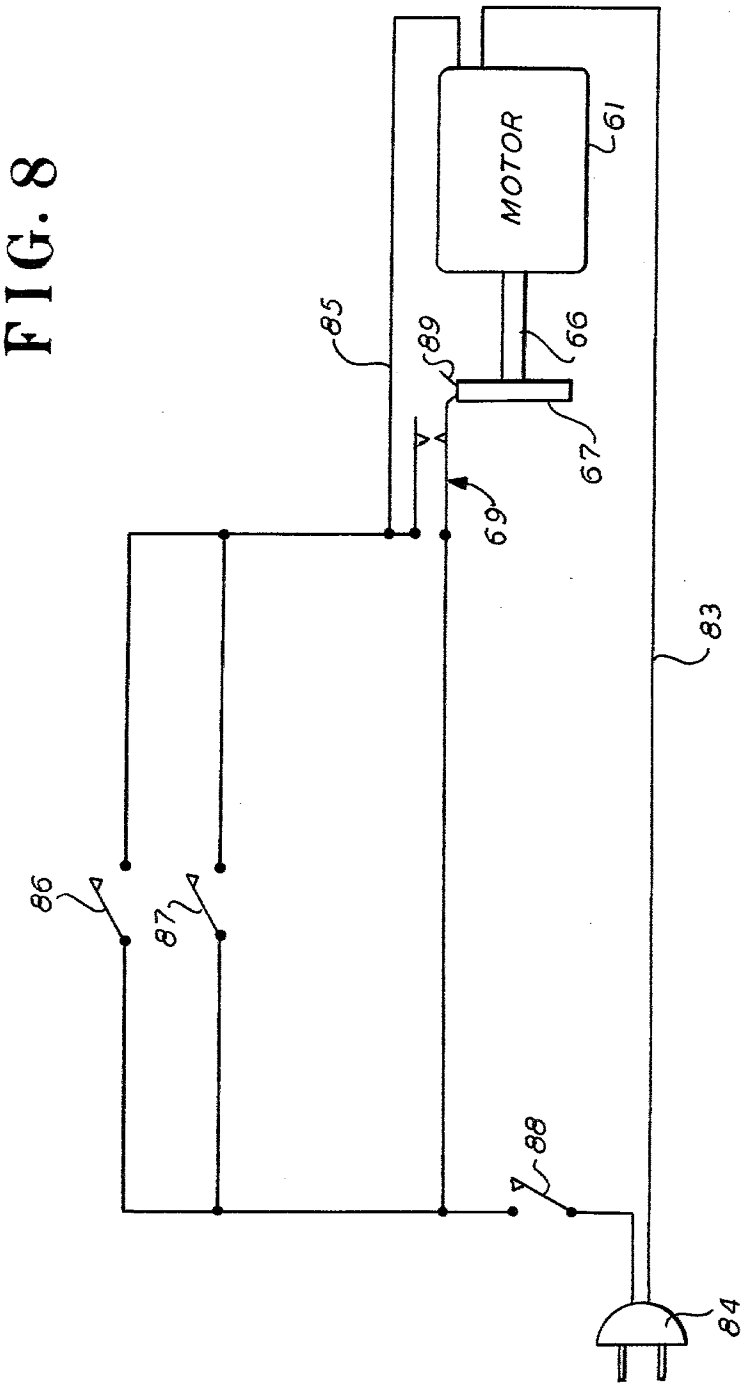
FIG. 8 is a schematic circuit diagram of the electric motor control means employed in the cocking device of the invention.

The motor control means utilized to actuate the motor means 51 is shown in FIG. 8 of the drawings wherein it is seen that the input of electric motor 61 has one side thereof coupled to one side of a voltage supply source (not shown) by means of a lead 83 and a plug 84 and the other side thereof coupled to the other side of the voltage supply source by a lead 85, a pair of manually-operable switches 86 and 87 which may comprise foot-operated switches and which are connected in parallel circuit, and a master, manually-operable disconnect switch 88. The master switch 88 may be conveniently mounted on the support bracket 52 as shown in FIG. 2 of the drawings. As illustrated, the switches 86,87, 88 and 89 are normally-open switches. The cam follower switch 69 is connected in parallel-circuit with the foot-operated switches 86 and 87, so that the three, parallel-connected switch means are connected in series-circuit with the master disconnect switch 88 and the motor input across the voltage supply source. It will be seen that with the master disconnect switch 88 in a closed position, the closure of any of switches 86, 87 and 69 will energize the motor 61 to cause the cam 67 to rotate. As the cam rotates, a cam follower or roller 89 which is mounted on the switch arm 90, as shown in FIG. 4 of the drawings, continuously engages the surface of the cam. With a cam configuration, as illustrated, wherein the cam is circular except for a single recessed area or depression 91, the cam follower switch 69 will be closed for all angular positions of the output shaft 66 of the motor means except the predetermined angular position in which the cam follower 89 becomes seated in the recessed area 91 to open the cam follower switch 69 and deenergize the electric motor 61. Accordingly, if either of the foot-operated switches 86 and 87 is closed momentarily, the motor 61 will be energized to rotate the cam 67 from the predetermined angular position at which the cam follower 89 is disposed in the cam depression 91, so that the motor will then become energized by a circuit completed through the cam follower switch 69. The motor will remain energized until the motor shaft and cam complete substantially one full revolution of 360°, at which time, the cam follower will again engage the depressed area 91 of the cam to open the circuit to the motor. With the foregoing arrangement, the disk member 68 will be driven through substantially one full revolution of 360° each time one of the foot switches 86 and 87 is closed by the foot of the chiropractor, so that the pelvic supports section 20 is cocked by closure of a foot switch. It will be apparent that different configurations of the cam and follower switch could be employed to achieve the same operation. For example, the cam 67 could again be substantially circular but have a projecting portion instead of the depressed portion 91, so that if a normally closed cam follower switch was utilized, the switch contacts would be closed during the time the cam follower engaged the circular portion of the cam and would be opened when the cam follower was actuated by the projecting portion on the cam. It may also be noted that the foot-operated switches 86 and 87 could be replaced by other types of switches, such as a knee-operated switch, for example, since this type of switch would also permit the pelvic section to be cocked without use of the practitioner's hands.

The automatic cocking device of the invention has a gentle cocking action which will not injure or alarm the patient. The gentle cocking action results from the eccentric linkage comprising the rotatable disk 68, the pin 72 and the connecting member 73 because, for a uniform rate of angular rotation of the disk 68 starting from the angular position shown in FIG. 4 of the drawings, the linear motion of the end of the chain 73 which is mounted on the crank 76 will slowly increase from a minimum to a maximum linear speed as the disk rotates from 0° to 90°, and will then decrease until the minimum linear speed is reached again at the 180° rotation point of the disk. Additionally, it is seen in FIGS. 1, 2 and 4 of the drawings that the automatic cocking device of the invention will not interfere with normal operation of the chiropractic table because the support bracket 52 on which the motor means 51 is mounted extends downwardly and away from the abdominal support section 18 so that this support member may be moved as desired to accomodate a particular patient or treatment. The support bracket 52, motor means 51, crank 76 and all of the mechanical and electrical components of the device except the foot-operated switches 86 and 87 are mounted on the laterally-extending support member 23 which is in turn mounted on the support rails 13, so that the automatic cocking device is free to rotate with the support frame and patient support sections about the central table shaft 14 when the patient is placed in a non-horizontal position. The automatic cocking device is not only suitable for factory installation on new chiropractic tables but is also adapted for field installation on existing chiropractic tables of the type having manually-rotatable cocking shafts. Such field installation is simplified because the support bracket 52 and the cross brace 57 may be mounted on the clevis members 24 and 25 usually found on existing tables. The clevis 25 shown in the drawings is formed with a special lug or projection 55 to accomodate the support bracket 52 and may replace the existing clevis on the table for field installation. The other required mechanical connection is the mounting of the crank 76 on the cocking shaft 35 by means of the clamps 77. It will be noted that such field installation of the automatic cocking device will not in any way impair the operation of the manual cocking device on existing chiropractic tables.

It is believed apparent that many changes could be made in the construction and described uses of the foregoing automatic cocking device and many seemingly different embodiments of the invention could be constructed without departing from the scope thereof. Accordingly, it is intended that all matter contained in the above description or shown in the accompanying drawings shall be interpreted as illustrative and not in a limiting sense.

What is claimed is:

1. In a chiropractic table of the type having a base, a support frame pivotally mounted on the base and a pelvic support section pivotally mounted on the frame for cocking to an elevated position by rotation of a cocking shaft through a predetermined angle of rotation and tripping to a dropped position by chiropractic pelvic thrusts, the combination comprising motor means mounted on the support frame, said motor means having a rotary output shaft;

lever means mounted on the cocking shaft for rotation thereof;

mechanical linkage means connected between said motor means shaft and said lever means for converting the rotary motion of the motor shaft to substantially unidirectional linear motion at the lever means to rotate the cocking shaft through the predetermined angle of rotation and cock the pelvic support section; and motor control means coupled to said motor means for starting and stopping said motor means to cock the pelvic support section.

2. The combination claimed in claim 1 wherein operation of said motor control means causes the output shaft of the motor means to rotate substantially through an angle of 360°, said lever means comprises a crank having one end thereof mounted on the cocking shaft and the other end thereof disposed a distance from the cocking shaft, and said mechanical linkage means is an eccentric comprising a rotatable disk member having an eccentrically mounted pin thereon, said disk member being connected to the output shaft of said motor means for rotation thereby, and a longitudinally-extending connecting member having one end thereof pivotally mounted on said pin and the other end thereof mounted on said other end of the crank.

3. The combination claimed in claim 2 wherein said longitudinally-extending connecting member comprises a flexible chain having one end thereof pivotally mounted on said pin and the other end thereof mounted on said other end of the crank, so that the eccentric is operable to cause unidirectional rotation of the cocking shaft in the direction required to cock the pelvic support section.

4. The combination claimed in claim 2 wherein said longitudinally-extending connecting member comprises a rod having one end thereof pivotally mounted on said pin and the other end thereof slidably disposed in an opening in said other end of the crank, and stop means mounted on said other end of the rod to prevent said other rod end from being pulled through said opening upon operation of the eccentric, so that the eccentric is operable to cause unidirectional rotation of the cocking shaft in the direction required to cock the pelvic support section.

5. The combination claimed in claim 2 wherein said motor means comprises electric motor means, and said motor control means comprises electric circuit means coupled to said electric motor means for control thereof and adapted to be coupled to a voltage supply source for energization thereby, said electric circuit means having manually-operable switch means for energizing said electric motor means to cause rotation of said motor means output shaft, and positive-responsive switch means responsive to the angular position of said motor means output shaft for deenergizing said motor means at a predetermined angular position of said motor means output shaft, so that said motor means output shaft makes substantially one full revolution of 360° after energization of the motor means by said manually-operable switch means.

6. The combination claimed in claim 5 wherein said manually-operable switch means is coupled in series-circuit with said electric motor means across the voltage supply source, and said position-responsive switch means comprises a cam follower switch coupled in parallel-circuit with said manually-operable switch means, and a rotatable cam for controlling the operation of said cam follower switch, said cam being mounted on said motor means output shaft for rotation therewith and having a configuration which actuates said cam follower switch at said predetermined angular position of the motor means output shaft, so that said electric motor means is energized through said cam follower switch for all angular positions of the motor means output shaft except said predetermined angular position.

7. The combination claimed in claim 5 wherein said one end of the crank is provided with clamping means for mounting said one crank end on the cocking shaft of the table, and said electric motor means is mounted on a support bracket having means thereon for mounting the bracket on the support frame of the table, so that said combination is adapted for field installation on chiropractic tables of the type having a manually-operable cocking shaft.

8. The combination claimed in claim 6 wherein said manually-operable switch means comprises a foot-operated switch.

9. The combination claimed in claim 6 wherein said manually-operable switch means comprises a pair of foot-operated switches coupled in parallel-circuit with said cam follower switch, and said electric circuit means includes a master manually-operable disconnect switch coupled in series circuit with said electric motor means and said parallel-coupled foot operated switches.

10. The combination claimed in claim 6 wherein said electric motor means comprises an electric motor having a rotatable output shaft, and a speed-reducing gear train connected between said electric motor output shaft and said rotatable disk member of the eccentric, to thereby reduce the speed at which the pelvic support member is cocked.

11. A cocking device for chiropractic tables of the type having a pivotally mounted pelvic support section adapted to be cocked to an elevated position by rotation of a cocking shaft through a predetermined angle of rotation and tripped to a dropped position by chiropractic pelvic thrusts comprising electric motor means adapted to be mounted on the table, said motor means having a rotary output shaft;

a crank having one end thereof adapted to be mounted on the cocking shaft for rotation of the cocking shaft;

an eccentric linkage having a rotatable disk member mounted on the motor means output shaft for rotation thereby, said disk member having a pin eccentrically mounted thereon, and connecting means having one end thereof pivotally mounted on said pin and the other end thereof mounted on the other end of said crank for unidirectionally transmitting the reciprocating component of motion of the pin to said other end of the crank to rotate the cocking shaft through the predetermined angle of rotation; and motor control means controlled by foot-operated switch means for energizing said motor means to cause the output shaft thereof to make a single revolution of substantially 360° in response to actuation of the switch means, to thereby cock the pelvic support section.

* * * * *

UNITED STATES PATENT OFFICE
CERTIFICATE OF CORRECTION

Patent No. 4,245,626 Dated January 20,1981

Inventor(s) Charles M. Paolino

It is certified that error appears in the above-identified patent and that said Letters Patent are hereby corrected as shown below:

Column 1, line 44, delete "patient-" and insert ---patient's---;
Column 1, line 62, delete "imited" and insert --limited--;
Column 3, line 42, delete "now" and insert --not--;
Column 4, line 15, delete "unitl" and insert --until--;
Column 4, line 27, delete "30" and insert --39--;
Column 6, line 2, delete "45" and insert --35--;
Column 6, line 60, delete "89" and insert --69--; and
Column 7, line 12, delete "and" and insert --or--.

In the Claims:

Column 9, line 32, delete "positive" and insert --position--.

Signed and Sealed this

*Sixteenth* Day of *June 1981*

[SEAL]

*Attest:*

RENE D. TEGTMEYER

*Attesting Officer* *Acting Commissioner of Patents and Trademarks*